United States Patent [19]

Owens

[11] Patent Number: 5,630,959

[45] Date of Patent: May 20, 1997

[54] MICROWAVABLE HEATING PAD FOR WARMING FOOD AND METHOD

[75] Inventor: Byron C. Owens, Asheboro, N.C.

[73] Assignee: Vesture Corporation, Asheboro, N.C.

[21] Appl. No.: 517,293

[22] Filed: Aug. 21, 1995

Related U.S. Application Data

[63] Continuation of Ser. No. 224,569, Apr. 7, 1994, abandoned, which is a continuation-in-part of Ser. No. 136,021, Oct. 14, 1993, Pat. No. 5,500,010, which is a continuation of Ser. No. 85,570, Jun. 30, 1993, Pat. No. 5,300,105, which is a continuation of Ser. No. 871,826, Apr. 21, 1992, abandoned, which is a continuation of Ser. No. 643,344, Jan. 22, 1991, abandoned, which is a continuation-in-part of Ser. No. 486,806, Feb. 26, 1990, abandoned.

[51] Int. Cl.[6] ................................................. H05B 6/80
[52] U.S. Cl. ................. 219/730; 219/759; 99/DIG. 14; 426/107; 426/234; 426/243
[58] Field of Search ........................... 219/730, 759, 219/734; 99/DIG. 14; 426/107, 109, 234, 243

[56] References Cited

U.S. PATENT DOCUMENTS

| | | |
|---|---|---|
| 1,927,751 | 9/1933 | Mensi . |
| 2,203,591 | 6/1940 | Brown . |
| 2,438,643 | 3/1948 | Moore . |
| 2,515,298 | 7/1950 | Fledman . |
| 2,675,630 | 4/1954 | Youmans . |
| 3,082,611 | 3/1963 | Alvis et al. . |
| 3,521,310 | 7/1970 | Greenawalt . |
| 3,611,455 | 10/1971 | Gottfried . |
| 3,872,525 | 3/1975 | Lea et al. ............................ 5/348 |
| 3,885,403 | 5/1975 | Spencer ........................... 62/530 |
| 3,946,188 | 3/1976 | Derby ............................. 219/730 |
| 4,123,855 | 11/1978 | Thedford . |
| 4,249,319 | 2/1981 | Yoshida . |
| 4,283,427 | 8/1981 | Winters et al. ................... 426/107 |
| 4,425,917 | 1/1984 | Kuznetz .......................... 128/403 |
| 4,488,552 | 12/1984 | McCann et al. .................. 128/402 |
| 4,499,131 | 2/1985 | Knox ................................ 428/68 |
| 4,561,441 | 12/1985 | Kolodziej . |
| 4,580,393 | 4/1986 | Furukawa ......................... 3/512 |
| 4,594,492 | 6/1986 | Maroszek ....................... 219/730 |
| 4,604,987 | 8/1986 | Keltner ........................... 126/204 |
| 4,671,267 | 6/1987 | Stout ............................... 128/156 |
| 4,694,829 | 9/1987 | Frye . |
| 4,743,726 | 5/1988 | Hughes et al. ................. 219/10.55 |
| 4,756,311 | 7/1988 | Francis, Jr. ...................... 128/403 |
| 4,841,646 | 6/1989 | Maurer, Jr. ........................ 36/2.6 |
| 4,849,593 | 7/1989 | Hughes et al. ................. 219/10.55 |
| 4,868,898 | 9/1989 | Seto . |
| 4,914,717 | 4/1990 | Gibbon .......................... 219/10.55 |
| 4,920,964 | 5/1990 | Francis, Jr. . |
| 4,931,608 | 6/1990 | Bills ............................... 219/759 |
| 4,933,193 | 6/1990 | Fisher ............................. 426/107 |
| 4,942,634 | 7/1990 | Saloff et al. ....................... 5/450 |
| 4,983,798 | 1/1991 | Eckler et al. .................... 219/759 |
| 5,035,241 | 7/1991 | Walasek et al. .................. 128/403 |
| 5,038,779 | 8/1991 | Barry et al. ..................... 128/402 |

(List continued on next page.)

OTHER PUBLICATIONS

Footwear described in pending patent application, serial No. 08/173,869, filed 02 Feb. 1994.

Therapeutic pad described in pending patent application, serial No. 08/085,570, filed 30 Jun. 1993.

Prior art pad.

Therapeutic pad shown in Figs. 1–5 of this patent application.

Pending patent application, serial No. 08/144,345, filed 01 Nov. 1993.

Concurrently filed patent application, for Ser. #08/224,552 Seat Cushion with Removable Heating Pad and Method.

*Primary Examiner*—Philip H. Leung

[57] ABSTRACT

A microwavable pad for heating food has a liquid absorbent to prevent liquid leakage in the event that the sealed thermoplastic envelope of the pad is ruptured. The method of forming the pad includes evacuating air from the thermoplastic envelope prior to sealing. The pad can be used alone or with a food cover to provide warmth and impart heat to food when the pad is placed in a container with the food.

13 Claims, 4 Drawing Sheets

U.S. PATENT DOCUMENTS

| | | |
|---|---|---|
| 5,050,598 | 9/1991 | Tucker . |
| 5,052,369 | 10/1991 | Johnson .................................. 126/400 |
| 5,070,223 | 12/1991 | Colasante ............................... 219/759 |
| 5,094,238 | 3/1992 | Gibbon .................................... 128/403 |
| 5,150,707 | 9/1992 | Anderson ................................ 128/402 |
| 5,230,170 | 7/1993 | Dahle . |
| 5,230,333 | 7/1993 | Yates et al. . |
| 5,260,536 | 11/1993 | Peery ...................................... 219/730 |
| 5,277,180 | 1/1994 | Angelillo et al. . |
| 5,300,105 | 4/1994 | Owens . |
| 5,331,688 | 7/1994 | Kiyohara . |
| 5,339,541 | 8/1994 | Owens . |
| 5,357,693 | 10/1994 | Owens . |
| 5,366,491 | 11/1994 | Ingram et al. . |

MICROWAVABLE HEATING PAD FOR WARMING FOOD AND METHOD

This is a file wrapper continuation of application Ser. No. 08/224,569, filed 7 Apr. 1994 now abandoned, which was a continuation-in-part of application Ser. No. 08/136,021, filed 14 Oct. 1993 U.S. Pat. No. 5,500,100, which was a continuation of application Ser. No. 08/085,570, filed 30 Jun. 1993, now U.S. Pat. No. 5,300,105, which was a continuation of Ser. No. 07/871,826, filed 21 Apr. 1992, now abandoned, which was a continuation of Ser. No. 07/643,344, filed 22 Jan. 1991, now abandoned, which was a continuation-in-part of Ser. No. 07/486,806, filed 26 Feb. 1990, now abandoned.

BACKGROUND OF THE INVENTION

1. Field of the Invention

The invention relates to microwavable pads and specifically to pads and a method for applying heat to food items to keep the food warm and appetizing for extended periods of time.

2. Description of the Prior Art and Objectives of the Invention

It is well known that liquid-containing microwavable therapeutic pads are designed for heating and cooling applications for parts of the human body, such as a bruised arm, thigh or back muscle or to relieve pain from a sprained ankle. Such therapeutic heating pads may contain liquids, such as in conventional hot water bottles, or may be more modern sealed liquid pouches that can be microwaved and then applied to sore muscles or joints. In recent years, microwavable pads have been manufactured and sold consisting of flexible plastic envelopes in which water-type solutions are contained. A pad is placed in a vacuum pump in which the air within the bag is withdrawn and the bag is then heat sealed with the liquid therein. Pads that have been used in the past to contain liquids for either heating or cooling have been susceptible to breakage and rupturing; consequently, the user's clothes, furniture, bed sheets and the like have become damaged, requiring disposal or at least cleaning. Bread baskets have been used for many years with cloth or other coverings to maintain warmth of the bread or other foods contained therein; however, such food can become cool relatively quickly and hence, unappetizing.

Thus, with the known problems and disadvantages associated with prior art microwavable pads, the present invention was conceived and one if its objectives is to provide a food container with a pad that is constructed to prevent leaks, even in the event the outer envelope of the pad is ruptured.

It is yet another objective of the present invention to provide a food warming pad and method for forming the same in which the pad has a liquid absorbent into which, in the event of seal breakage, the liquid will be absorbed and will substantially remain within the envelope.

It is yet another objective of the present invention to provide a microwavable pad that is vacuum formed and that contains a liquid and a liquid absorbent, whereby the liquid absorbent is in a resilient compressed state.

It is yet another objective of the present invention to provide a method for easily forming a microwavable pad that, in the event of rupture, will aid in preventing food damage and injury to fabric or other materials against which it is placed, due in part to an improved moisture impervious covering.

It is also an objective of the present invention to provide a microwavable pad that includes a readily visible temperature indication device, which will provide additional safety and efficiency in heating the pad.

Another objective of the present invention is to provide a temporary food container and food covering having a microwavable pad to help keep food warm before serving commences.

Various other objectives and advantages of the present invention become apparent to those skilled in the art as a more detailed description of the embodiments is presented below.

SUMMARY OF THE INVENTION

In view of the aforesaid objectives, the invention herein provides a new and improved apparatus and method for keeping food warm, which solves many problems of conventional methods that are now being used. The microwavable pad of the invention is formed from a permanently sealed, thin, flexible outer envelope, and included therein is a liquid filled absorbent, such as a synthetic sponge, which is compressed prior to envelope sealing. The compressed sponge retains liquid, and, in the event the envelope is accidentally punctured, the sponge will rapidly enlarge in size, preventing any liquid within the pouch from escaping through the rupture. The method of forming the pad includes placing a liquid-containing thermoplastic envelope in a vacuum chamber apparatus. A sponge is inserted into the liquid; thereafter, by the use of a vacuum pump, air is evacuated from the envelope, the sponge being compressed as the envelope deflates. Once a sufficient vacuum is pulled, for example, 24 inches of Hg., the envelope is sealed by a pair of heating elements. The sealed envelope is placed in a water impervious envelope having a rubberized covering to increase the safety and durability. A sheet of insulating material is also placed in the water impervious envelope beneath the thermoplastic envelope. A thermochromic liquid crystal temperature indication device is affixed to the outer surface of the rubberized covering to indicate when the interior liquid has reached a sufficient temperature. The therapeutic pad is then ready to be placed in a fabric cover and may be microwaved or otherwise heated prior to use. Microwavable pads of the invention can be placed within a food-covering fabric, whereby food can be covered for insulation and heat retention purposes prior to serving.

DESCRIPTION OF THE PREFERRED EMBODIMENTS

Figure 8:
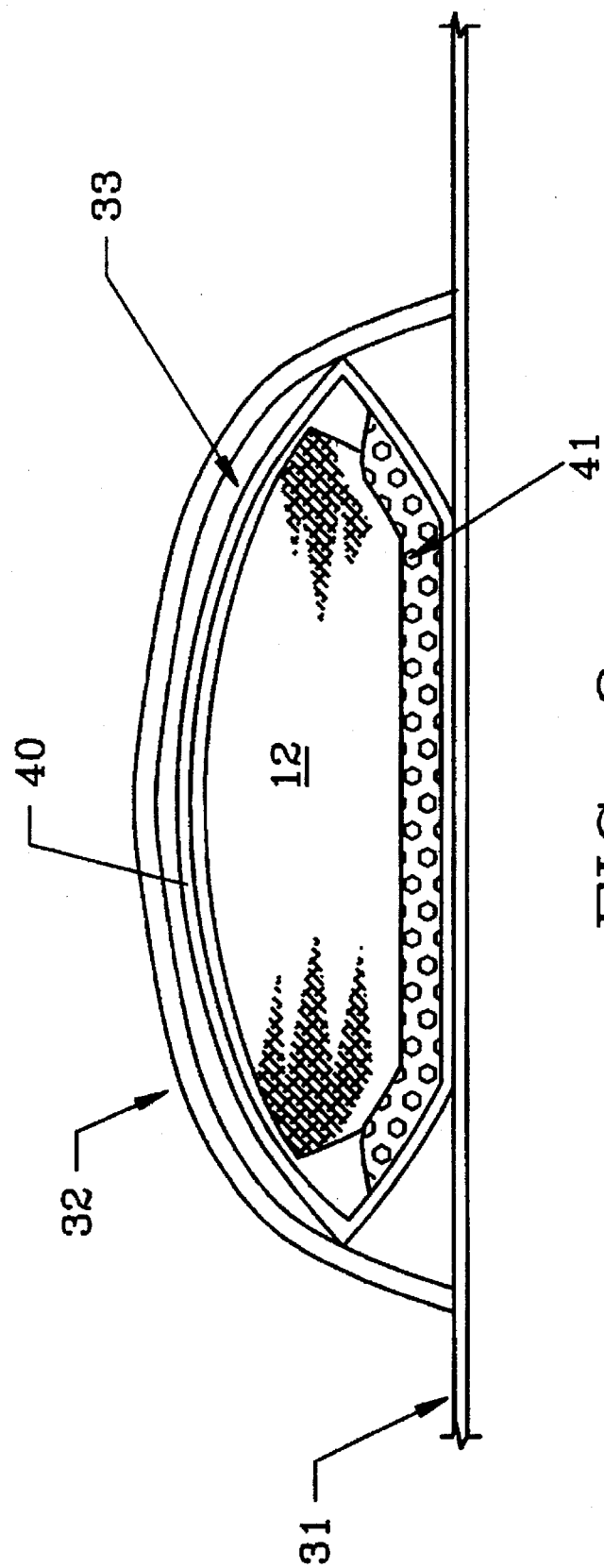
FIG. 8 depicts an end view of the food cover along lines 8—8, as seen in FIG. 7, with the heating pad shown in partial cross-section.

The preferred form of the microwavable pad of the invention is shown in partial cross-sectional view in FIG. 8 and includes a water impervious outer cover, a thermoplastic envelope Containing a liquid-filled sponge that has been compressed to approximately forty percent of its original size, and a sheet of insulating material within the water impervious cover beneath the thermoplastic envelope. The sponge compression provides unique features to the device for use in a variety of applications, whereby, in the event of an inadvertent rupture of the envelope, the sponge will expand and absorb any liquid which may otherwise drain through the rupture and contact human skin causing burns or irritations or stain food covers, food or the like. The insulating material prevents heat from escaping downwardly away from food to be warmed. The preferred method of forming the therapeutic pad comprises placing a flexible thermoplastic envelope, such as may be formed from polyethylene, in a conventional vacuum-forming and heat-sealing cabinet. Liquid is introduced into the envelope, a sponge also positioned therein. With the vacuuming device turned on, the air is pumped from the envelope; consequently, as the envelope collapses, the sponge is compressed. Once a sufficient vacuum has been drawn, such as twenty-four inches of Hg., as demonstrated on a vacuum gauge, the heat sealing elements are activated to permanently seal the envelope. It can then be placed with a sheet of insulating material into a rubberized covering and an exterior fabric cover for later microwaving and use in keeping food warm.

The preferred method of the invention utilizes a container comprising a typical bread basket in which a cloth cover with a pocket for retaining the microwavable pad is placed. The pad is heated in a standard microwave oven for about three minutes, after which it is removed and placed, insulated side down, into the central pocket of the flexible cloth food cover. The food cover is then placed in the basket with the pad along the inside bottom surface. Bread or the like is then placed in the basket, and the excess and ends of the cloth are folded over the bread, as typically done to keep the bread warm before and during meals. The pad will impart heat to the bread for several hours, usually much longer than the necessary time to consume most meals, even if the bread is left uncovered.

DETAILED DESCRIPTION OF THE DRAWINGS AND OPERATION OF THE INVENTION

Figure 1:
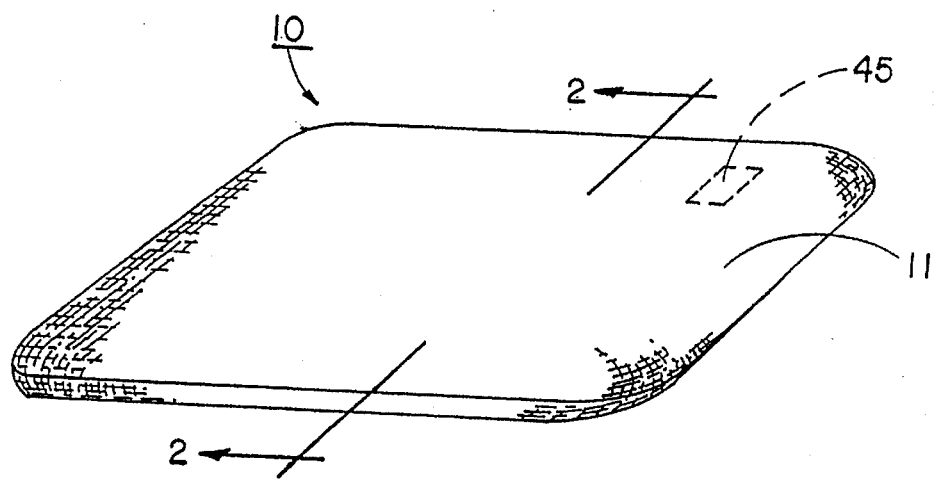
FIG. 1 illustrates a typical microwavable pad of the invention shown herein.

Turning now to the drawings, pad 10, as shown in FIG. 1, contains a liquid filled microwavable pad of the invention. The pad can be placed in a conventional microwave oven and heated for approximately five minutes. The pad is then removed and placed proximate food to provide warmth thereto.

Figure 2:
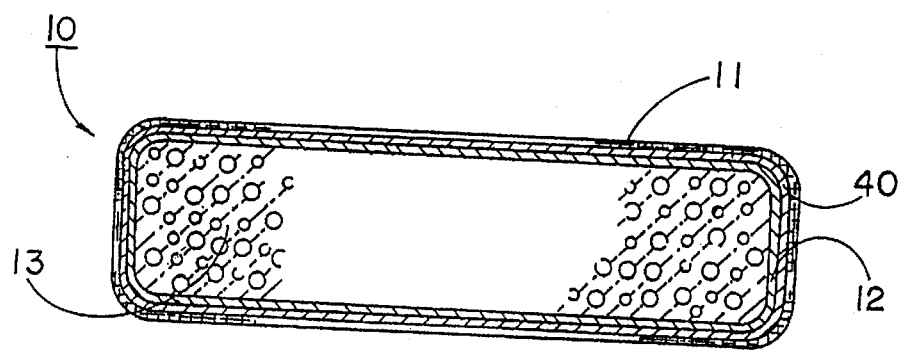
FIG. 2 demonstrates a cross-sectional view of the pad shown in FIG. 1 along lines 2—2.
Figure 3:
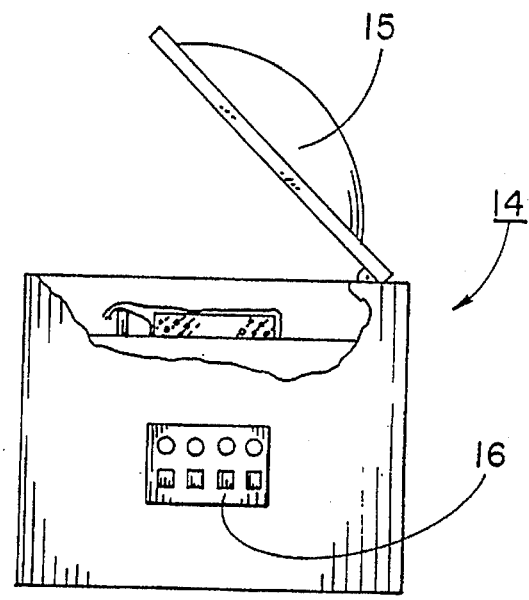
FIG. 3 pictures a conventional combination vacuum forming and heat sealing unit.

Pad 10 is shown in FIG. 2 in cross-sectional view, whereby cover 11 is formed from a cotton fabric and encloses sealed flexible plastic envelope 12, which may be, for example, formed from polyethylene or other suitable and durable plastics. Means 13 to absorb liquid is positioned within envelope 12 and in a compressed state, as will be hereinafter explained. Means 13 consists of a synthetic nylon sponge, although other resilient, compressible absorbents may also be used, such as natural sponges or other synthetic or natural structures. As seen in FIG. 2, means 13 is compressed to approximately forty percent of its normal size, and, as would be understood, if envelope 12 is ruptured, means 13 would attempt to recover to its normal, non-compressed configuration. Water impervious covering 40 is shown in FIGS. 2 and 3 and may consist of cotton flannel/rubberized sheathing, a neoprene coated nylon sheeting, a natural rubberized sheeting or other similar combinations. These materials are conventional and are commonly used in hospitals and for incontinence uses on beds, chairs and other articles. Their durability and high resistance to tearing and puncturing make them desirable; thus, they have been found to provide superior water impervious coatings for microwavable pads.

Figure 5:
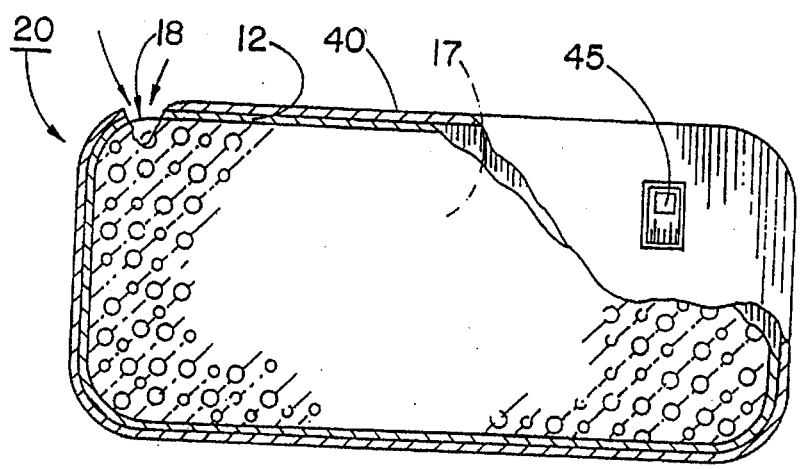
FIG. 5 illustrates expansion of the liquid absorbent, such as if a leak occurs in the envelope.
Figure 4A:
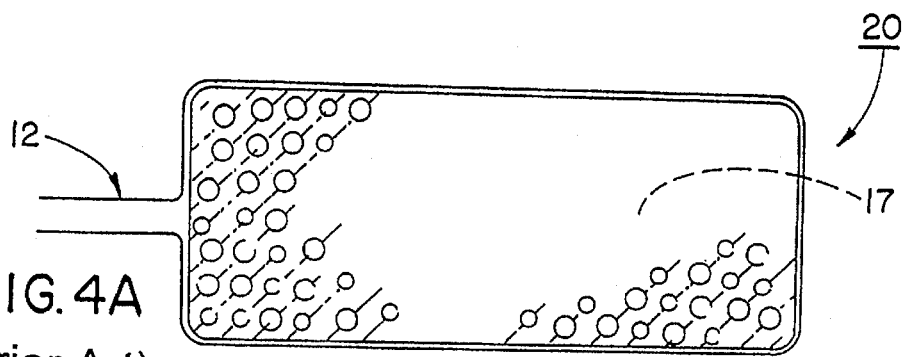
FIG. 4A depicts the envelope of the therapeutic pad having a liquid and a liquid absorbent therein prior to vacuuming.
Figure 4B:
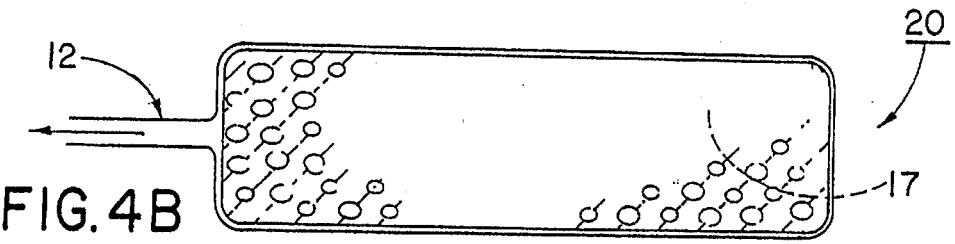
FIG. 4B illustrates the envelope of FIG. 4A but with a partial vacuum applied.
Figure 4C:
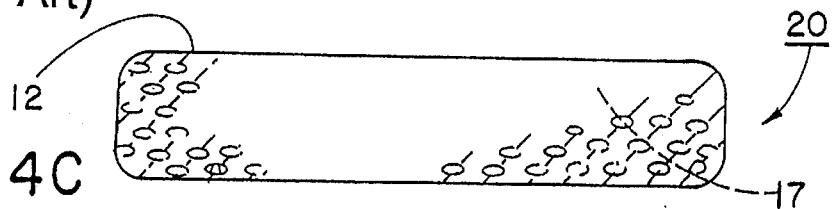
FIG. 4C shows the envelope, which has been fully vacuumed and sealed, prior to insertion into a rubberized covering.

In FIG. 3, combination vacuum and heat sealing device 14 is shown having a chamber lid 15 and control panel 16 for vacuum forming and heat sealing thermoplastic envelopes, such as envelope 12 shown in FIG. 2. Device 14 is conventional and is sold throughout the food industry for vacuum packaging meats and other products. In forming a microwavable pad as presented herein, empty envelope 12 is filled with a suitable amount of liquid, such as a water solution or proprietary formula, and sponge 17, as shown in FIG. 4A, is placed therein. As shown in FIGS. 4B and 4C, sponge 17 is reduced in size as air is evacuated from collapsing envelope 12, and, as would be understood in FIG. 4C, with sponge 17 substantially compressed once the vacuum pressure reaches the controlled level of, for example, 24 inches of Hg., envelope 12 is permanently heat sealed, maintaining sponge 17 in a compressed posture. Thereafter, cover 11 can be applied thereto as desired. In the event the seal of envelope 12 is broken or in the event envelope 12 is ruptured at some surface point, air, as depicted by the arrow in FIG. 5, will rush into envelope 12 allowing sponge 17 to expand and close off rupture 18 while absorbing any liquid that may attempt to drain therethrough. Hence, with the rupture so protected and filled with sponge 17, therapeutic pad 20 is safe for use in that it will not substantially cause injury, damage or staining. Water-impervious, rubberized covering 40 is shown in FIG. 5 surrounding envelope 12 to provide a more durable product. The aforementioned rubberized covering 40 may be formed from a cotton flannel, which is bonded to a natural or synthetic rubber, or may consist of nylon sheathing, which has been neoprene coated, as is well-known in the incontinence product art. Also in FIG. 5, liquid crystal temperature indicator 45 is shown positioned atop pad 20. Liquid crystal temperature indicating devices are old and have been used for many years to indicate temperatures and temperature changes. Temperature indicator 45 is affixed by an adhesive or by other means to rubberized covering 40 to assist one in determining the temperature and the time required to bring pad 20 to its desired temperature level in a microwave oven during heating. Thermochromic liquid crystal temperature indicator 45 consists includes a transparent, adhesive-backed base for attachment to covering 40. Affixed to the base is a polymer pouch for containing liquid crystals. Various temperature indicia are available, which may include a black background top surface at room temperature with white letters that indicate high, medium and low temperatures.

Figure 7:
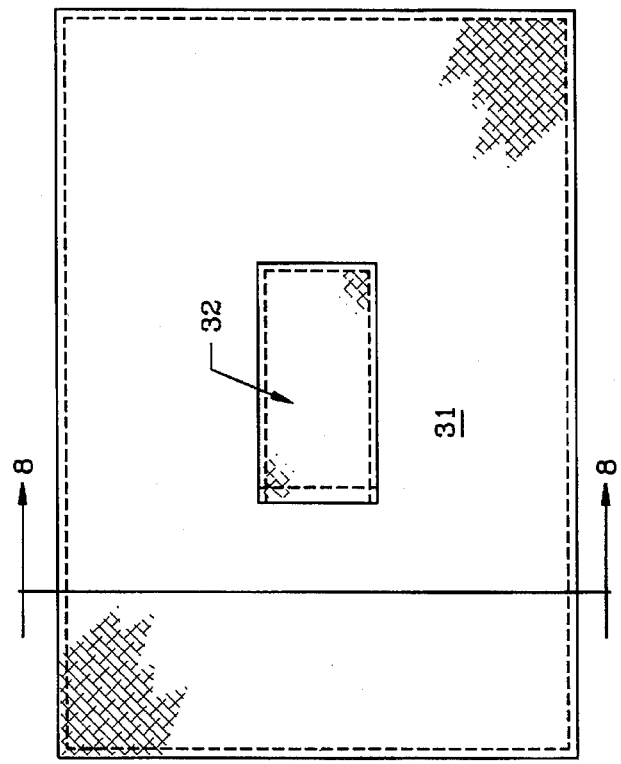
FIG. 7 demonstrates a top plan view of the food cover removed from the container.
Figure 6:
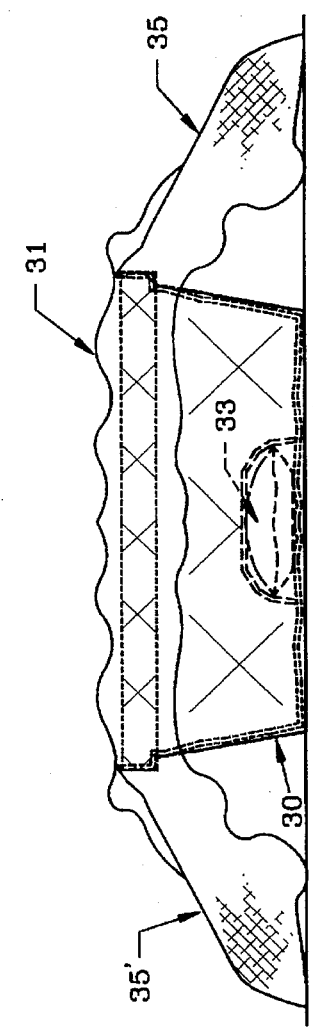
FIG. 6 presents an empty food container with a food cover and heating pad therein.
Figure 9:
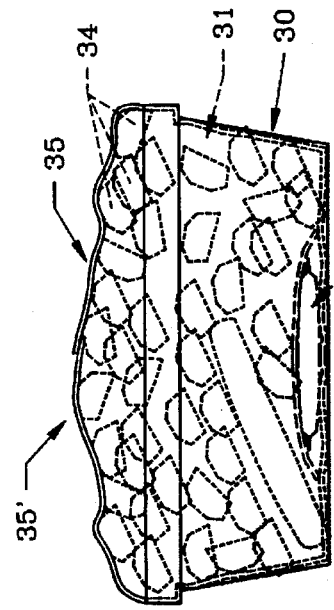
FIG. 9 shows the food container with food therein that is covered while heat from the heating pad is imparted thereto.

In FIG. 6, conventional food container 30 is shown consisting of a bread basket. Placed within food container 30 is flexible cloth food cover 31, which is dimensioned in excess of the interior of container 30. In FIG. 7, flexible cloth food cover 31 is shown removed from food container 30 and, as seen, is rectangular and includes central pocket 32 for microwavable pad 33, as seen in FIG. 8. FIG. 8 also shows microwavable pad 33 in partial cross-section. Sealed, flexible plastic envelope 12, which is the same as in FIG. 2, is placed above a layer of insulating material 41 inside water impervious covering 40. Insulating material 41 may be, for example, a ¼" thick layer of polystyrene foam and is approximately the same width as plastic envelope 12. Cloth food cover 31 is formed from a conventional textile fabric sheet, such as made from cotton, a cotton blend, a synthetic or a syntheic blend, and pocket 32 of the same fabric is sewn thereto, which provides a means for easily retaining microwavable pad 33. The size of cover 31 is in excess of the interior dimensions of food container 30 to allow food therein to be surrounded and covered along the sides and top. In FIG. 9, food 34, here seen consisting of conventional dinner rolls, has been placed in food container 30 and has been covered by excess ends 35, 35' of food cover 31. If desired, a lid (not shown) can also be placed on food container 30 to hold in more heat and moisture.

The method of the invention includes removing microwavable pad 33 from pocket 32 and placing it in a microwave oven for approximately five minutes on a high temperature setting. Pad 33 is then removed from the microwave oven and placed, insulated side down, within pocket 32, whereupon food cover 31 is then positioned along the bottom of food container 30 with excess ends 35, 35' extending therefrom, as seen in FIG. 6. Thereafter, rolls 34 or other food objects are placed on top of pocket 32 within container 30, and ends 35, 35' are folded over rolls 34; as a result, heat is imparted from pad 33 to keep rolls 34 at a warm, appetizing temperature. Other breads or foods may likewise be warmed or held warm for extended periods of time (several hours) without undue inconvenience.

The illustrations and examples provided herein are for explanatory purposes only and are not intended to limit the scope of the appended claims.

I claim:

1. Heating apparatus for a food item comprising: a planar cloth food cover, said planar food cover consisting of a single ply, a removable liquid-containing microwavable heating pad, said planar food cover comprising means to retain said heating pad, said retaining means located centrally of said planar food cover, said planar food cover having length and width exceeding the length and width of said retaining means, said heating pad positioned within said retaining means, whereby food placed on said retaining means can be warmed by said heating pad and enclosed by said planar food cover.

2. Heating apparatus as claimed in claim 1 wherein said retaining means comprises a pocket.

3. Heating apparatus as claimed in claim 2 wherein said pocket defines an opening.

4. Heating apparatus as claimed in claim 1 wherein said planar food cover is rectangular.

5. A method of imparting heat to a food item enclosed within a single-ply planar cloth food cover, comprising the steps of:

(a) heating a liquid-containing pad by microwave radiation;

(b) positioning said heated pad centrally of said planar food cover;

(c) placing said food item proximate the heated pad; and (d) enclosing said food item within said planar food cover to impart heat thereto.

6. The method of claim 5 wherein the step of heating a pad by microwave radiation comprises:

(a) placing said pad inside a microwave oven; and (b) irradiating said pad.

7. The method of claim 5 wherein the step of positioning the heated pad centrally of said planar food cover comprises placing said pad into a pocket located centrally of said planar food cover.

8. The method of claim 5 wherein the step of placing the food items proximate the heated pad comprises:

(a) placing the heated pad into a food container; and (b) placing the food items into the food container atop the heated pad.

9. The method of claim 8 wherein the step of placing the food items into the food container comprises placing the food items into a bread basket.

10. Heating apparatus in which a microwavable pad is releasably contained within a single-ply planar cloth food cover in combination with a food container, the combination comprising: means to retain said microwavable pad, said retaining means attached to said planar food cover, said retaining means located centrally of said planar food cover, said retaining mean& having lesser length and width than said planar food cover, said heating pad positionable within said retaining means, said planar food cover placed within said food container whereby said microwavable pad will impart heat to food items placed therein.

11. The combination of claim 10 wherein said microwavable pad comprises a liquid.

12. The combination of claim 10 wherein said retaining means comprises a pocket.

13. The combination of claim 12 wherein said pocket defines an opening.

* * * * *